United States Patent
Mahato et al.

(10) Patent No.: US 7,320,890 B2
(45) Date of Patent: Jan. 22, 2008

(54) SOLUBLE STEROIDAL PEPTIDES FOR NUCLEIC ACID DELIVERY

(75) Inventors: Ram I. Mahato, Memphis, TN (US); Anurag Maheshwari, Salt Lake City, UT (US); Sung Wan Kim, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 315 days.

(21) Appl. No.: 11/099,999

(22) Filed: Apr. 5, 2005

(65) Prior Publication Data

US 2005/0287671 A1 Dec. 29, 2005

Related U.S. Application Data

(62) Division of application No. 10/482,721, filed as application No. PCT/US02/21265 on Jul. 3, 2002, now Pat. No. 6,875,611.

(60) Provisional application No. 60/302,725, filed on Jul. 3, 2001.

(51) Int. Cl.
   *C12N 15/85* (2006.01)
(52) U.S. Cl. .................. 435/320.1; 536/23.5; 536/24.1
(58) Field of Classification Search ...................... None
   See application file for complete search history.

(56) References Cited

U.S. PATENT DOCUMENTS 6,008,202 A    12/1999  Huang et al.
6,696,038 B1 *  2/2004  Mahato et al. ............. 424/1.45
6,875,611 B2   4/2005  Mahato et al.

OTHER PUBLICATIONS

Cotten, Langle0Rouault, Kirlappos, Wagner, Mechtler, Zenke, Beug, and Birnstiel, Transferrin-polycation-mediated introduction of DNA into human leukemic cells: Stimulation by agents that affect the survival of transfected DNA or modulate transferrin receptor levels, Proc. Natl. Acad. Sci, USA, Jun. 1990, pp. 4033-4037, vol. 87.

Han, Mahto, and Kim, Water-Soluble Lipopolymer for Gene Delivery, Bioconjugate Chem., 2001, 12, pp. 337-345.

\* cited by examiner

*Primary Examiner*—James Ketter
(74) *Attorney, Agent, or Firm*—Clayton, Howarth & Cannon, P.C.

(57) ABSTRACT

Amphiphilic lipopeptide compositions for gene delivery are disclosed. An illustrative amphiphilic lipopeptide composition includes a human protamine 2 peptide conjugated to a hydrophobic moiety. Illustrative hydrophobic moieties include sterols, bile acids, and fatty acids. The amphiphilic lipopeptide composition is mixed with a nucleic acid such that the nucleic acid binds to the peptide portion of the lipopeptide. This mixture is placed in contact with mammalian cells to effect transfection of the cells with the nucleic acid. A method of making such amphiphilic lipopeptides is also described.

1 Claim, 8 Drawing Sheets

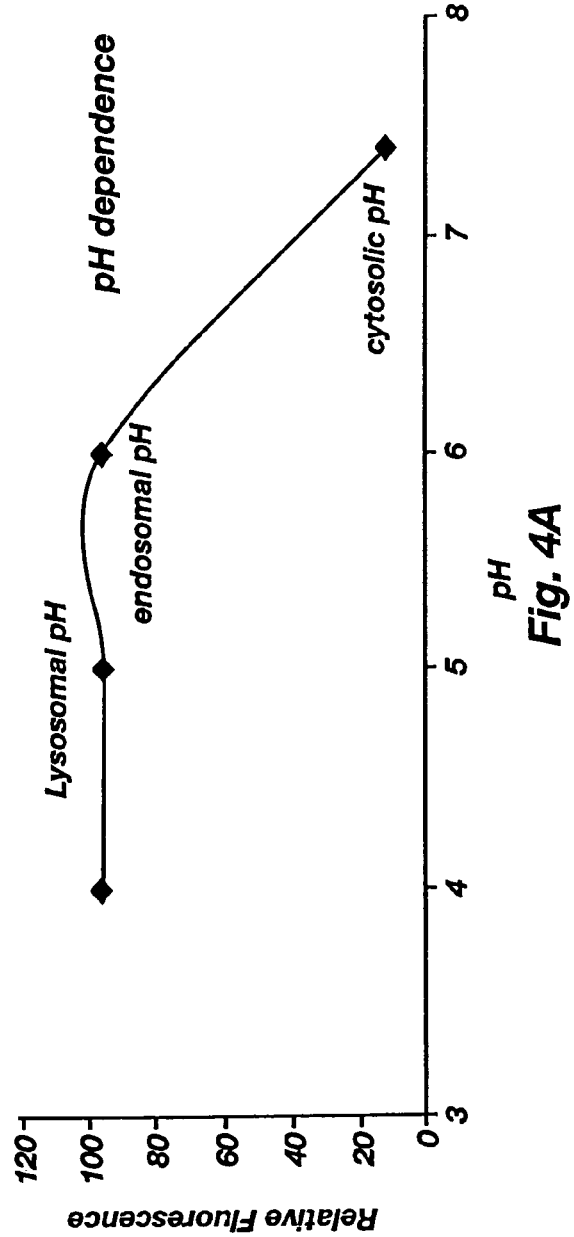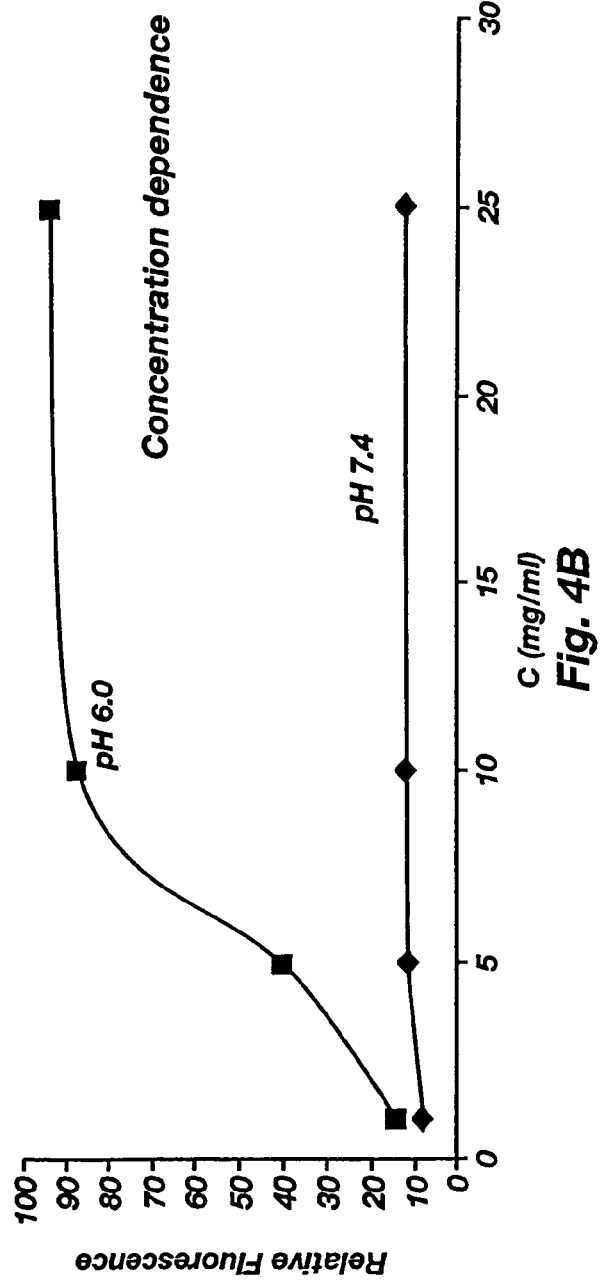

SOLUBLE STEROIDAL PEPTIDES FOR NUCLEIC ACID DELIVERY

CROSS-REFERENCE TO RELATED APPLICATIONS

This application is a division of U.S. application Ser. No. 10/482,721, filed Jan. 2, 2004, now U.S. Pat. No. 6,875,611, which was the National Stage of International Application No. PCT/US02/21265, filed Jul. 3, 2002, which was published in English under PCT Article 21(2), which claims the benefit of U.S. Provisional Application No. 60/302,725, filed Jul. 3, 2001, all of which are hereby incorporated by reference in their entireties.

STATEMENT REGUARDING FEDERALLY SPONSORED RESEARCH OR DEVELOPEMENT

Not applicable

BACKGROUND OF THE INVENTION

This invention relates to gene delivery. More particularly, this invention relates to compositions of matter and methods of use and making thereof for gene delivery wherein the compositions of matter comprise amphiphilic lipoproteins configured for binding nucleic acids.

Progress in the area of gene delivery has been tremendous in the last several years, yet in clinical settings the dream of a successful therapy based on nucleic acids remains a frustrating riddle. Gene delivery vectors have been largely put into either of two categories, viral or non-viral, and most of the published reports have focused on circumventing the deficiencies inherent in both types of vectors. Factors such as toxicity, permanently altering the host genome through recombination events with viral vectors, and poorly optimized delivery capabilities with non-viral vectors demand application of concepts that have clinical relevance in terms of safety, efficacy, and patient compliance. However, by now its clear that feasibility of a single vector serving as a universal gene carrier for all disease targets is remote and impractical.

In cancer immunotherapy, for example, the use of cytokines such as interleukin-12, which is a proven anti-proliferative cytokine in confinement and inhibition of tumor progression and metastasis in several types of cancers in vivo, is of great interest. Although cytokine gene therapy has been attempted with a variety of viral vectors, such as adenovirus, retrovirus, adeno-associated viruses, and lentiviruses, there is still a growing need to optimize non-viral gene carriers with unprecedented safety and efficacy profiles. Among existing non-viral gene carriers polyethyleneimine, and lipid-protamine-DNA (LPD) lipoplexes have had some success in terms of cytokine gene transfer efficiency, however the issues related to carrier-associated toxicities are poorly understood. Cationic lipids are water insoluble and require the formation of liposomes using a colipid, such as dioleyl phosphatidylethanolamine (DOPE) or cholesterol in presence of organic solvents, which involves multiple steps. Although their gene transfer applications have been under investigation since 1987, the exact mechanism elucidating their structure-function relationship has not been completely revealed. It is believed that lipid anchors, such as steroids and fatty acid chains, serve to provide amphiphilic character to these carriers, which would orient the head group surface charge more favorably, and also take part in hydrophobic interactions with plasma and organelle membranes. Lipid anchors can also interact specifically with various membrane receptors for enhanced cellular uptake and lipid-mediated transduction. Polyethyleneimine and Starburst™ dendrimers, due to their high transfection efficiency, have received a lot of attention and remain, by far, the most effective cationic polymers for transfection created to date. The functioning of these polymers has been attributed to the so-called proton sponge effect due to secondary and tertiary amines present in these polymers, which supposedly leads to disruption inside endosomes and endo-lysosomes by osmotic swelling. Gene carriers that would combine the concepts of water solubility, amphiphilic nature, lipid mediated membrane interactions, endosomal buffering, and nuclear targeting would be an exciting option for plasmid based gene therapy.

Peptide based gene delivery systems are least investigated, and their applications in delivering cytokine genes are virtually unexplored. Several different types of peptides that possess endosomolytic, fusogenic, or membrane permeabilizing properties derived from various viruses, such as vesicular stomatitis virus glycoprotein (VSVG) and influenza virus hemaglutinin, have been used either alone or in combination with liposomes and polymers. Co-polymers of lysine and histidine have also been shown to efficiently deliver genes inside cells, and this property has been attributed to the imidazole ring of the histidine side chain, which behaves as an endosomal rupturing agent.

While prior compositions and methods for delivering peptides are known and are generally suitable for their limited purposes, they possess certain inherent deficiencies that detract from their overall utility. For example, polyethyleneimine is effective only in high molecular weight (>10,000 M.W.) formulations, but such high molecular weight compositions can be toxic, elicit immune responses, are non-biodegradable, are not site specific, and condense plasmid DNA too tightly. Cationic lipids can be toxic at therapeutic doses, elicit immune responses, require several steps to synthesize and involve the use of organic solvents, are water insoluble, offer little inherent endosomal buffering, and are not site specific. Current peptide-based gene carriers may be toxic at therapeutic doses, elicit immune responses, often require cationic lipids for effectiveness, frequently are subject to aggregation, and exhibit poor water solubility due to hydrophobic amino acid residues.

In view of the foregoing, it will be appreciated that providing compositions and methods for delivering peptides, especially cytokines, would be a significant advancement in the art.

BRIEF SUMMARY OF THE INVENTION

These and other objects can be addressed by providing a composition comprising a PRM2 peptide conjugated to a hydrophobic moiety. In one illustrative embodiment of the invention, the PRM2 peptide comprises a peptide identified herein as SEQ ID NO:2.

The hydrophobic moiety illustratively comprises a sterol, a bile acid, or a fatty acid. Illustrative sterols include cholestanol, coprostanol, cholesterol, epicholesterol, ergosterol, and ergocalciferol. Examples of bile acids include cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid. Examples of fatty acids include $C_4$-$C_{20}$ alkanoic acids, such as butyric acid, valeric acid, caproic acid, caprylic acid, capric acid, lauric acid, myristic acid, palmitic acid, and stearic acid.

In another illustrative embodiment of the invention, the PRM2 peptide is conjugated to the hydrophobic moiety through an amide (peptide) linkage. Other linkers known in the art may also be used according to the invention. The hydrophobic moiety can be conjugated to the PRM2 peptide through a non-terminal amino acid residue, thus forming a "T-shaped" conjugate.

Another illustrative embodiment of the invention comprises a mixture of a nucleic acid and a conjugate comprising a PRM2 peptide and a hydrophobic moiety. The nucleic acid binds to the PRM2 peptide portion of the conjugate. The nucleic acid can be a plasmid or other type of nucleic acid known in the art for gene delivery.

Still another illustrative embodiment of the invention comprises a method for transfecting a mammalian cell, such as a human cell, comprising contacting the cell with a composition comprising a mixture of a nucleic acid and a conjugate comprising a PRM2 peptide and a hydrophobic moiety, and then incubating the cell under conditions suitable for growth thereof.

Yet another illustrative embodiment of the invention comprises a plasmid configured for expressing p35 and p40 subunits of interleukin-12 under control of at least one cytomegalovirus promoter. An illustrative configuration of this plasmid is p2CMVmIL-12.

BRIEF DESCRIPTION OF THE SEVERAL VIEWS OF THE DRAWINGS

FIGS. 4A-B show membrane permeabilization of cultured CT-26 cells with the soluble steroidal peptide of FIG. 2 in the presence of ethidium bromide. FIG. 4A shows permeabilization as a function of pH, wherein as pH 5 and 6 less than 25% staining was observed. FIG. 4B shows permeabilization as a function of concentration of the soluble steroidal peptide.

DETAILED DESCRIPTION

Figure 1:
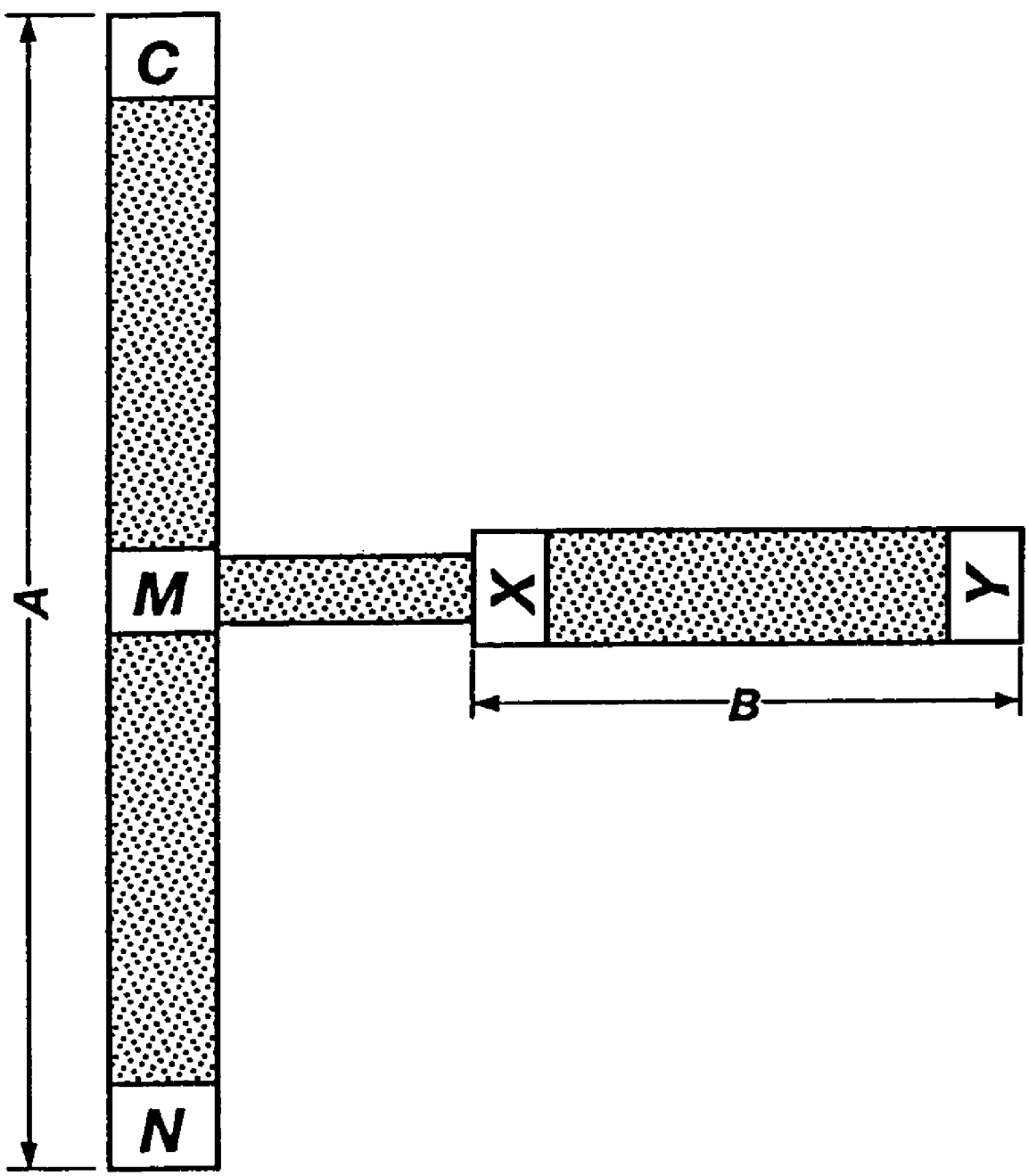
FIG. 1 shows a schematic representation of an amphiphilic lipopeptide according to the present invention.

Before the present compositions of matter, methods of making thereof, and methods of use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a composition comprising a mixture of "a conjugate" and "a nucleic acid" includes a mixture of two or more of such conjugates and/or two or more of such nucleic acids.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "peptide" means peptides of any length and includes proteins.

As used herein, "PRM2 peptide" means a peptide derivative of human protamine 2 and configured for binding to a nucleic acid. For example, amino acid residues 51-63 of human protamine 2 comprise the sequence identified herein as SEQ ID NO:1, which is rich in arginine and histidine residues, and binds to nucleic acids. In a PRM2 peptide according to the present invention, the cysteine residue of SEQ ID NO:1 was replaced with a lysine residue, and an additional histidine residue was added at both the amino and carboxy termini of SEQ ID NO:1 to result in the peptide identified as SEQ ID NO:2. The lysine residue provides an ϵ-amino residue for linkage to the hydrophobic moiety.

Thus, illustrative PRM2 peptides include the peptide having the amino acid sequence identified as SEQ ID NO:1 and biologically functional equivalents thereof, such as peptides having the amino acid sequence identified herein as SEQ ID NO:2. Such functional equivalents retain functionality in binding nucleic acids, although they may be truncations, deletion variants, or substitution variants of SEQ ID NO:1 or include additional amino acid residues attached thereto.

As mentioned above, changes may be made in the structure of the PRM2 peptide while maintaining the desirable nucleic acid-binding characteristics. For example, certain amino acid residues may be substituted for other amino acid residues in a protein structure without appreciable loss of interactive binding capacity with structures such as, i.e., antigen-binding regions of antibodies or binding sites of ligands such as an IL-2 receptor-binding peptide. Since it is the interactive capacity and nature of a protein that defines that protein's biological functional activity, certain amino acid sequence substitutions can be made in a protein sequence and nevertheless obtain a protein with like properties. It is thus contemplated that various changes may be made in the amino acid sequence of a PRM2 peptide without appreciable loss of its biological utility or activity.

It is also well understood by the skilled artisan that inherent in the definition of a biologically functional equivalent protein or peptide is the concept that there is a limit to the number of changes that may be made within a defined portion of the molecule and still result in a molecule with an acceptable level of equivalent biological activity. It is also well understood that where certain residues are shown to be particularly important to the biological or structural properties of a protein or peptide, e.g. residues in active sites, such residues may not generally be exchanged.

Amino acid substitutions are generally based on the relative similarity of the amino acid side-chains relative to, for example, their hydrophobicity, hydrophilicity, charge, size, and the like. An analysis of the size, shape, and type of the amino acid side-chains reveals, for example, that arginine, lysine, and histidine are all positively charged residues; that alanine, glycine, and serine are all a similar size; and that phenylalanine, tryptophan, and tyrosine all have a generally similar shape. Therefore, based upon these considerations, the following conservative substitution groups or biologically functional equivalents have been defined: (a) Cys; (b) Phe, Trp, Tyr; (c) Gln, Glu, Asn, Asp; (d) His, Lys, Arg; (e) Ala, Gly, Pro, Ser, Thr; and (f) Met, Ile, Leu, Val. M. Dayhoff et al., Atlas of Protein Sequence and Structure (Nat'l Biomed. Res. Found., Washington, D.C., 1978).

To effect more quantitative changes, the hydropathic index of amino acids may be considered. Each amino acid has been assigned a hydropathic index on the basis of its hydrophobicity and charge characteristics, which are as follows: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. J. Kyte & R. Doolittle, A simple method for displaying the hydropathic character of a protein, 157 J. Mol. Biol. 105-132 (1982). It is known that certain amino acids may be substituted for other amino acids having a similar hydropathic index or score and still retain a similar biological activity. In making changes based on the hydropathic index, the substitution of amino acids whose hydropathic indices are within ±2 is desired, within ±1 is particularly desired, and within ±0.5 is even more particularly desired.

It is also understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is desired, within ±1 is particularly desired, and within ±0.5 is even more particularly desired.

As used herein, "hydrophobic moiety" means a hydrophobic entity that can be conjugated to a hydrophilic peptide for obtaining an amphiphilic composition. Illustrative hydrophobic moieties according to the present invention include steroids, such as sterols and bile acids, and fatty acids. Illustrative sterols that can be used in the present invention, either as is or after activation to permit more facile conjugation to a hydrophilic peptide, include cholestanol, coprostanol, cholesterol, epicholesterol, ergosterol, ergocalciferol, and the like. Illustrative bile acids that can be used in the present invention, either as is or after activation to permit more facile conjugation to a hydrophilic peptide, include cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and the like. Illustrative fatty acids that can be used in the present invention, either as is or after activation to permit more facile conjugation to a hydrophilic peptide, include C4 to C20 alkanoic acids, such as butyric acid, valeric acid, caproic acid, caprylic acid, capric acid, lauric acid, myristic acid, palmitic acid, stearic acid, and the like.

FIG. 1 shows a schematic representation of an amphiphilic lipopeptide according to the present invention. The amphiphilic lipopeptide includes a hydrophilic peptide head group, represented by A, which is conjugated to a hydrophobic entity, represented by B. The hydrophilic peptide is coupled to the hydrophobic entity by a linker, represented by L, which can be any of a variety of linkers known in the art for linking chemical subunits together into a whole unit, such amide linkages, including peptide linkages, urethane linkages, disulfide linkages, ether linkages, and the like. The amino- and carboxy-termini of the hydrophilic peptide are represented by N and C, respectively. Illustratively, the hydrophobic entity is linked to the hydrophilic peptide through a non-terminal amino acid residue, represented by M, thus conferring on the amphiphilic lipopeptide a "T-shaped" configuration. FIG. 1 also shows that the hydrophobic entity can be linked through certain moieties thereof. For example, in the case where the hydrophobic entity is a steroid, the $C_1$-$C_5$ end of the steroid, represented by X, may be illustratively linked to the peptide, and the $C_{22}$-$C_{27}$ end of the steroid, represented by Y, is not directly linked to the peptide. Other configurations are also possible within the scope of the present invention, however, as is exemplified in the examples below. By way of further example, in the case where the hydrophobic entity is a fatty acid, the carboxylic acid end of the fatty acid, represented by X, is linked to the peptide, and the carbon chain end of the fatty acid, represented by Y, is not directly linked to the peptide.

EXAMPLE 1

Synthesis, Purification, and Physicochemical Characterization

Figure 2:
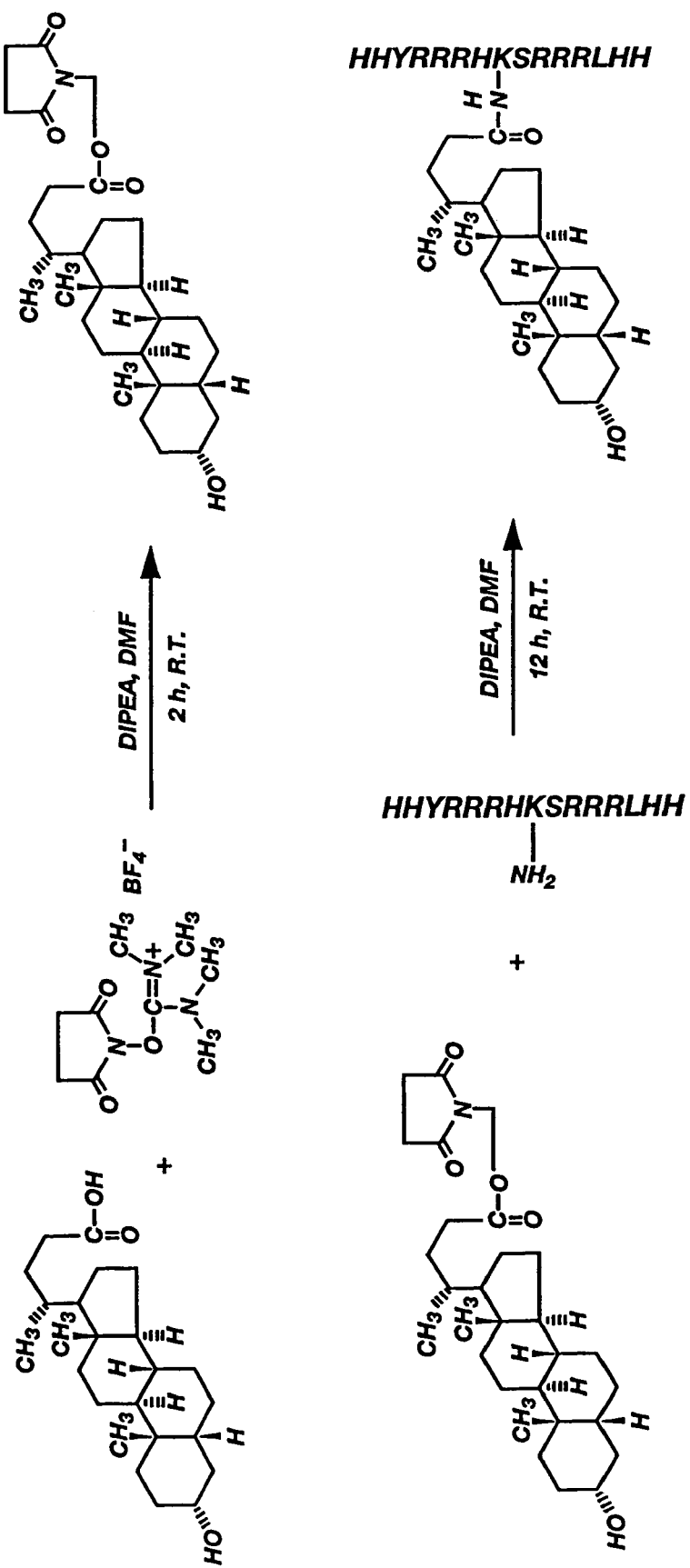
FIG. 2 shows a schematic representation of synthesis of an illustrative soluble steroidal peptide according to the present invention.

The hydrophilic peptide head group of an illustrative amphiphilic lipopeptide, SSP, is based on the peptide sequence His-Tyr-Arg-Arg-Arg-His-Cys-Ser-Arg-Arg-Arg-Leu-His (SEQ ID NO:1) corresponding to amino acid residues 51-63 of human protamine 2 (PRM2), which is rich in arginine and histidines. The cysteine residue at amino acid 57 amino acid was replaced with lysine for providing an $\epsilon$-amino group for linkage to a hydrophobic moiety, and an additional histidine residue was included on both the N-terminus and the C-terminus to yield the peptide chain His-His-Tyr-Arg-Arg-Arg-His-Lys-Ser-Arg-Arg-Arg-Leu-His-His (SEQ ID NO:2). The entire synthesis scheme is shown in FIG. 2.

Figure 3:
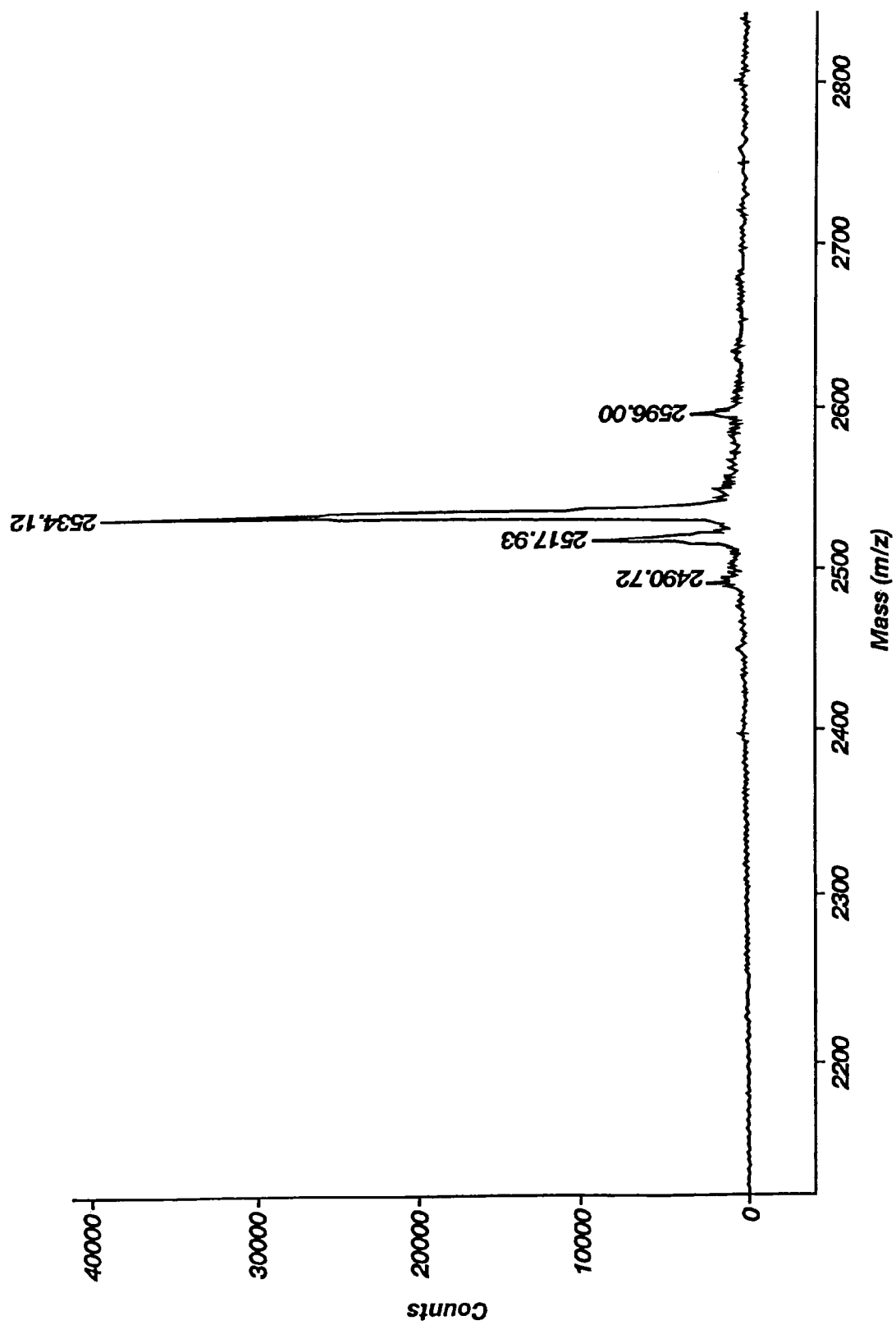
FIG. 3 shows a mass spectrum of the illustrative soluble steroidal peptide of FIG. 2; a major peak is at 2315.22, which corresponds to the molecular weight of this soluble steroidal peptide, and minor peaks are evident at 2272.13, 2332.08, and 2394.96, which account for <5% impurities.

The peptide $H_2N$-His-His-Tyr-Arg-Arg-Arg-His-Lys-Ser-Arg-Arg-Arg-Leu-His-His-COOH (SEQ ID NO:2) was synthesized by solid phase method on rink amide resin using the standard 9-fluorenylmethoxycarbonyl (Fmoc) strategy on an Applied Biosystems 433A peptide synthesizer. 2,2,4,6,7-Pentamethyl-dihydrobenzofurane-5-sulfonyl (Pbf), Trityl (Trt) and 1-(4,4-dimethyl-2,6-dioxocyclohexylidene) 3-methylbutyl (ivDde) were used as protective groups for arginine, histidine and lysine side chains, respectively, and for other amino acids, tertiary-butoxycarbonyl (t-Boc) was used as the protecting group. After synthesis, the peptide attached to the resin was briefly treated with 5% trifluoroacetic acid to remove the Dde protective group from the $\epsilon$-amine of lysine side chains. It was then washed multiple times with 100% methanol to obtain approximately 50 µM of peptide for further reactions. Activated steroid was prepared as follows: 30.105 mg of O-(N-Succinimidyl)-N,N,N',N'-tetramethyluronium tetrafluoroborate (TSTU, Aldrich, Milwaukee, Wis.) was dissolved in 100 µl of dimethyl formamide (DMF), 174.2 µl of pure diisopropyl ethylamine (DIPEA, Sigma Chemical Co., St. Louis, Mo.) was dissolved in 825.8 µl of DMF, and 376.58 mg of lithocholic acid (LA, Aldrich, Milwaukee, Wis.) was dissolved in 1 ml DMF to obtain their 1 Molar solutions. The TSTU solution (100 µl) was gradually dispensed in 100 µl of LA solution in the presence of 3 fold molar excess of DIPEA and then allowed to react for a period of 2 hours at room temperature with mild shaking. The reaction mixture was then allowed to react with the peptide in a total reaction volume of 2 ml for 12 hours at room temperature with shaking. The reaction mixture was washed several times with DMF followed by deprotection with 95% trifluoroacetic acid (TFA, Aldrich, Milwaukee, Wis.) for a period of 90 minutes at room temperature. The supernatant solution was separated from the resin after centrifugation at 1000 g. The final reaction yield was >80% with respect to starting amounts of peptide. The deprotected steroidal peptide was purified using reverse phase HPLC on a Vydac C18 column (4.6×250 mm with 2×20 guard). The purified soluble steroidal peptide (SSP) was >93% pure and its composition was confirmed by amino acid analysis. The trifluoroacetic acid attached to the SSP was replaced by acetic acid and lyophilized until further use. SSP was characterized using Matrix Assisted Laser Desorption Ionization Time Of Flight (MALDI-TOF) mass spectrometry (m/z=2534.12; FIG. 3). The concentration of SSP was determined by using $\epsilon_{274.5}$ of 1400 $M^{-1}$ $cm^{-1}$ for un-ionized tyrosine side chain and was reconstituted in water at a concentration of 10 mg/ml until further use.

EXAMPLE 2

The procedure of Example 1 was followed except that 413.7 mg of cholesteryl carboxylic acid (CA) was substituted for lithocholic acid.

Cholest-5-ene-3β-carboxylic acid (CCA) was synthesized as follows. A solution of methyl magnesium iodide was prepared under reflux by pouring 25 ml tetrahydrofuran (THF) on 400 mg Mg turnings with a pinch of iodine and a few drops of $CH_3I$ in a 3-neck flask for 10 min. After the vigorous reaction subsided, a solution of 4 g 3β-chlorocholest-5-ene in 50 ml THF was added drop wise over a period of 3 hours. After refluxing for 3 hours, the reaction was cooled to room temperature. To this mixture was poured finely ground dry ice (10 g), followed by stirring for 1 hour. This solution was cooled in an ice bath and hydrolyzed by adding ice cold 1 M $H_2SO_4$ (100 ml). After stirring for 5 min, 10 g NaCl and 100 ml diethyl ether were added. The layers were separated, and then the aqueous layer (bottom layer) was again extracted with diethyl ether (100 ml). The combined organic (ethereal) layers were washed 5 times with a solution of $Na_2S_2O_3.5H_2O$ (120 mg) in $H_2O$ (30 ml) to remove a persistent orange color. Finally the organic layer was washed with double-distilled $H_2O$ (30 ml) several times. The organic layer was filtered to remove the suspension of bicholesteryl. The filtrate was then dried with $MgSO_4$ and again filtered. The organic layer was concentrated in vacuum and vacuum dried for 18 hours. The crude solid was triturated with ice-cold hexanes (3×50 ml). The solid was vacuum dried for 1 h. The product obtained (0.5 g, 12.5% yield) was ~90% pure and was used for further reactions as such.

EXAMPLE 3

Membrane Permeabilization Study

Membrane permeabilization studies were performed to find out whether SSP was able to form pores through plasma membranes and whether this phenomenon had any pH dependence or not. SSP prepared according to Example 1 was used at micromolar concentrations on cells preincubated with ethidium bromide, which intercalates between the strands of dsDNA and causes it to fluoresce. Ethidium bromide on its own is a poor membrane permeant, however, if the membranes are permeabilized, it would rapidly cross the cytoplasm, accumulate in the nucleus, and bind to the cellular DNA. Its fluorescent property would allow us to thus find the extent to which permeabilization via SSP occurred.

The membrane permeabilization activity of SSP was determined using flow cytometry. CT-26 cells were grown overnight and at 70-80% confluency were trypsinized and centrifuged. Cells were washed several times in 1×PBS (pH 7.4) and eventually resuspended in it to make cell suspensions of 1×10⁶ cells/ml. One microliter of ethidium bromide (10 mg/ml) was mixed in 0.5 ml of cell suspension aliquots and stored at 4° C. 15 minutes before use. The pH of cell suspensions was adjusted to values 5,6,7, or 8 using either 1N NaOH or 1N HCl solutions 5 minutes before starting the experiment. SSP was finally used to permeabilize the membranes at the same final concentration for pH studies or at different concentrations at pH 7.4. Temperature effects at 4°

C. and 37° C. were also studied to find any temperature dependent differences in permeabilization. After 5 and 15 minutes incubation, the cell fluorescence intensity was measured using FACScan Analyzer (Becton Dickinson, Sunnyvale, Calif.), which has a single 15-mW argon (488 nm) laser light source. A 585 nm long pass filter was used to collect the emitted red fluorescence. The forward scatter, side scatter, and ethidium bromide fluorescence were simultaneously recorded with 10,000 cells at 300 events per second. The results were later analyzed using cell quest software provided by the same manufacturer. Histogram statistics were used to quantitatively determine the extent of permeabilization.

FIG. 4A shows the pH dependence and the time dependence of the extent of permeabilization when 10 µM SSP was used at pHs 5, 6, 7 and 8. At pHs above the pKa of the imidazole ring of histidine (pKa=6.1), there was poor fluorescence and very few cells (<25%) were stained. However, at lower pHs, such as 5 and 6, the cells were stained rapidly, within a period of 5 minutes, and over 97% cells were stained. FIG. 4B shows the fluorescent staining of genome at different concentrations of SSP. High levels of staining (>85%) were achieved when cells were incubated with 5 µM of SSP or above, and almost 100% staining levels were achieved at 10 µM SSP and above. These results indicate that SSP facilitates rapid diffusion in a concentration dependent fashion, which occurs only at pHs where imidazole ring of histidine is completely deprotonated.

EXAMPLE 4

Secondary Structure of SSP

It was desirable to find out whether SSP showed any secondary structures in solutions with different pHs and, if so, to determine the pattern of change with decreasing values of pH. Circular dichroism (CD) measurements were performed at 25° C. at pH 5, 6, 7, and 8 using an Aviv 62DS spectrometer (Aviv Associates, Lakewood, N.J.) and a 0.1 cm pathlength quartz cuvette. SSP concentration used in each case was 25 µM. Wavelength scans at 1 nm bandwidth, 1 nm per step with 5 s data averaging for each sample were repeated 4 times and later, averaged and corrected by buffer baseline spectrum. Peptide alone was also used as control to distinguish between the SSP and peptide and any likely contributions by steroid anchor.

Figure 5:
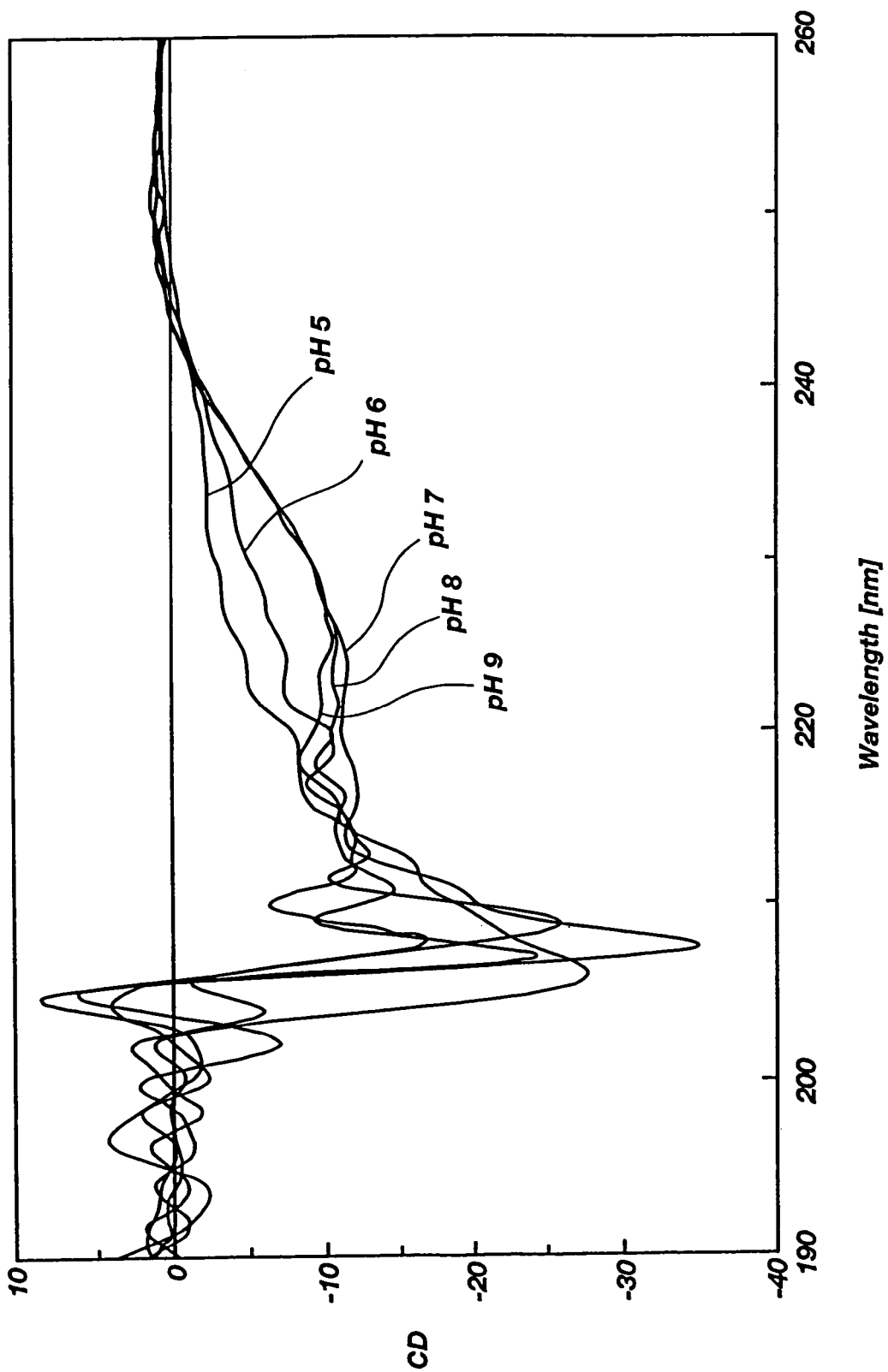
FIG. 5 shows a circular dichroism spectrum of the soluble steroidal peptide of FIG. 2.

FIG. 5 shows the circular dichroism wavelength scans from 195 nm to 280 nm for SSP at various pHs, and, as expected, SSP did not show any secondary structure. For comparisons, the same peptide sequence (SEQ ID NO:2) was used in control experiments to account for any structural changes induced by the steroid anchor. However, no significant secondary structure formation was found. This could be explained by the fact that SSP contained mainly arginines and several histidines. Positively charged arginines would have mutual electrostatic repulsion and would project an extended conformation in solution, which would retain SSP as a T-shape molecule. This type of structure proves two things. First, the membrane permeabilization could be mainly due to deprotonated histidine residues, and there was no contribution due to any changes in the secondary conformations of SSP such as change in the α-helical structure which is reminiscent of the way some viral peptide sequences work to permeabilize plasma membranes and endosomal compartments. Second, the extended sequence of SSP would provide maximum exposure of arginines to negatively charged phosphodiester bonds thus minimizing the amount of SSP needed to condense the pDNA into small particles. T-shaped cationic amphiphiles have also been shown to facilitate much higher gene expression compared to conventional I-shaped amphiphiles.

EXAMPLE 5

Condensation with DNA, Particle Size, and Zeta Potential

SSP was characterized in terms of condensation with plasmid DNA, particle size, and zeta potential.

IL-12 is a heterodimeric cytokine encoded by two separate genes, p40 and p35. It is naturally produced by macrophages and B lymphocytes. Plasmid p2CMVmIL-12 was constructed with each subunit-encoding gene under the transcriptional control of a separate cytomegalovirus (CMV) promoter, which has been described previously. Briefly, EcoRI and XmaI restriction enzyme sites were introduced into the p35 and p40 cDNAs by polymerase chain reaction using pCAGGS-IL12 as a template. After PCR reactions, the p35 and p40 cDNAs were purified by 1% agarose gel electrophoresis and electroelution. The purified cDNAs were digested with EcoRI and XmaI and inserted into pCI plasmid (Promega, Madison, Wis.), resulting in construction of pCMV-p35 and pCMV-p40, respectively. The expression unit of p40 in pCMV-p40 was then isolated by digestion with Bgl II and BamHI, followed by 1% agarose gel electrophoresis. The isolated p40 expression unit was inserted at the BamHI site of pCMV-p35. The resulting plasmid, p2CMVmIL-12 was confirmed by restriction enzyme assays. A plasmid encoding luciferase under control of a simian virus 40 (SV40) promoter, (pGL3-control vector, hereinafter, "pLuc") was used as a reporter gene and was purchased from Promega (Madison, Wis.). Plasmids were amplified using the DH5α strain of *E. coli* (Promega, Madison, Wis.) and purified using EndoFree™ Qiagen Kit (Qiagen, Boulder, Colo.) following the manufacturer's protocols. Plasmids were characterized by UV spectrophotometric assay at 260/280 nm and 0.7% agarose gel electrophoresis to determine the purity, integrity and concentration of the plasmids; restriction enzyme assay to confirm that there was no rearrangement of the genes during cloning and propagation. The optical density ratios at 260 nm to 280 nm of these plasmid preparations were in the range of about 1.7 to 1.8.

Various formulations of SSP/p2CMVmIL-12 were prepared as follows: 100 µL aliquots of SSP at various concentrations and pDNA (0.2 mg/ml) were prepared in 4.5% (w/v) glucose to bring the osmolality to 285-295 mOsm, and 1M phosphate buffer was used to bring the pH to 8.0 of both aliquots. SSP/pDNA complexes at various N/P ratios ranging from 0.5/1 (N/P) to 50/1 (N/P) were prepared by rapidly mixing contents of SSP aliquot in pDNA aliquots using a pipettor. N/P ratio was calculated by taking into account 3 nitrogens for each arginine in SSP, thereby resulting in 18 nitrogens for each SSP molecule. The SSP/pDNA complexes were incubated for 15 minutes at room temperature before electrophoresis.

ζ-potential and particle size of PAGA/plasmid complexes were measured as follows: SSP/pDNA complexes were prepared and then diluted in 3.8 ml of 0.1 µm filtered water to bring the volume to 4 ml. The samples were subjected to mean particle size measurement using ZetaPALS (Brookhaven Instruments Corp, Holtsville, N.Y.). Following the determination of particle size, the samples were evaluated for their electrophoretic mobility by the same equipment using the same light source and wavelength. All experiments were performed at 25° C. and 677 nm wavelength at a constant angle of 15°. The ζ potential was automatically calculated from the electrophoretic mobility based on Smoluchowski's equation. The particle size was reported as effective mean diameter.

SSP condensed pDNA completely at N/P ratios 3/1 and above under the aforementioned formulation conditions. The SSP/pDNA complexes resulted in small particle size in the range of 136 nm to 56 nm for N/P ratios ranging from 5/1 to 50/1. The guanidinium group of arginine remains protonated across pH range 1-13 and provides efficient pDNA condensation in strongly buffered solutions. The SSP/pDNA complexes were stable for about 1-2 weeks and did not show any signs of aggregation or change in surface charge which was confirmed by a repeat of particle sizing, zeta potential, and gel electrophoresis. It is envisaged that small size SSP/pDNA complexes would enable higher levels of intratumoral dispersibility after local administration as well as efficient cellular uptake through endocytosis.

The exact mechanisms governing nucleocytoplasmic trafficking are not clearly known, however, it is likely that after events such as cellular uptake, endocytosis and yet unknown mechanisms the SSP/pDNA complexes will remain in cytoplasm before nuclear translocation of pDNA. SSP and pDNA alone were also tested for their cytosolic stability. To study the stability of SSP/p2CMVmIL-12 complexes inside cytoplasm, these complexes were incubated them with cytosolic extract and the results indicate that pDNA was stable for long periods of time when complexed with SSP. The problems encountered during pDNA transfer are greatly influenced by cytosolic nucleases and SSP was able to protect the pDNA against these nucleases. This would increase the probability of nuclear translocation of intact plasmid leading to increase in the levels of gene expression. Since SSP has mostly amide bonds which connect individual amino acids as well as the headgroup and steroid anchor, it would be stable enough for the time period required for protecting and facilitating the pDNA into the nucleus but would eventually degrade into biologically safe metabolites.

EXAMPLE 6

Cytotoxicity Assay

Cytotoxicity of SSP/p2CMVmIL-12 complexes prepared at different N/P ratios were assessed using an MTT assay. CT-26 colon adeno-carcinoma cells were grown and maintained in RPMI 1640 medium (GIBCO-BRL, Gaithersburg, Md.), which was supplemented with 10% fetal bovine serum (FBS), 100 U/ml penicillin, 100 U/ml streptomycin and 50 µg/ml gentamycin (all from Gibco-BRL, Gaithersburg, Md.) at 37° C. and humidified 5% $CO_2$.

Briefly, CT-26 cell lines were seeded in 96 well plates at 4000 cells/well and incubated for 24 hours. After checking the cell confluency, which was over 80%, SSP/p2CMVmIL-12 complexes prepared at N/P ratios ranging from 5/1 to 100/1 were added to the cells at a dose of 0.15 µg pmIL-12/well. Following 48 hrs of incubation, 25 µl of 5 mg/ml 3-[4,5-dimethylthiazol-2-yl]-2,5-diphenyltetrazolium bromide (MTT, Sigma Chemical Co., St. Louis, Mo.) stock solution in phosphate buffered saline (PBS, Gibco-BRL) was poured into each well reaching a final concentration of 0.5 mg/ml MTT. The plate was then incubated at 37° C. in 5% $CO_2$ for 4 hrs. The medium was removed and 150 µl of dimethyl sulfoxide (DMSO, Aldrich) was added to dissolve the formazan crystals. The plate was read spectrophotometrically at 570 nm in an ELISA plate reader. The relative cell viability was calculated as $[Abs]_{sample}/[Abs]_{control} \times 100$.

Figure 6:
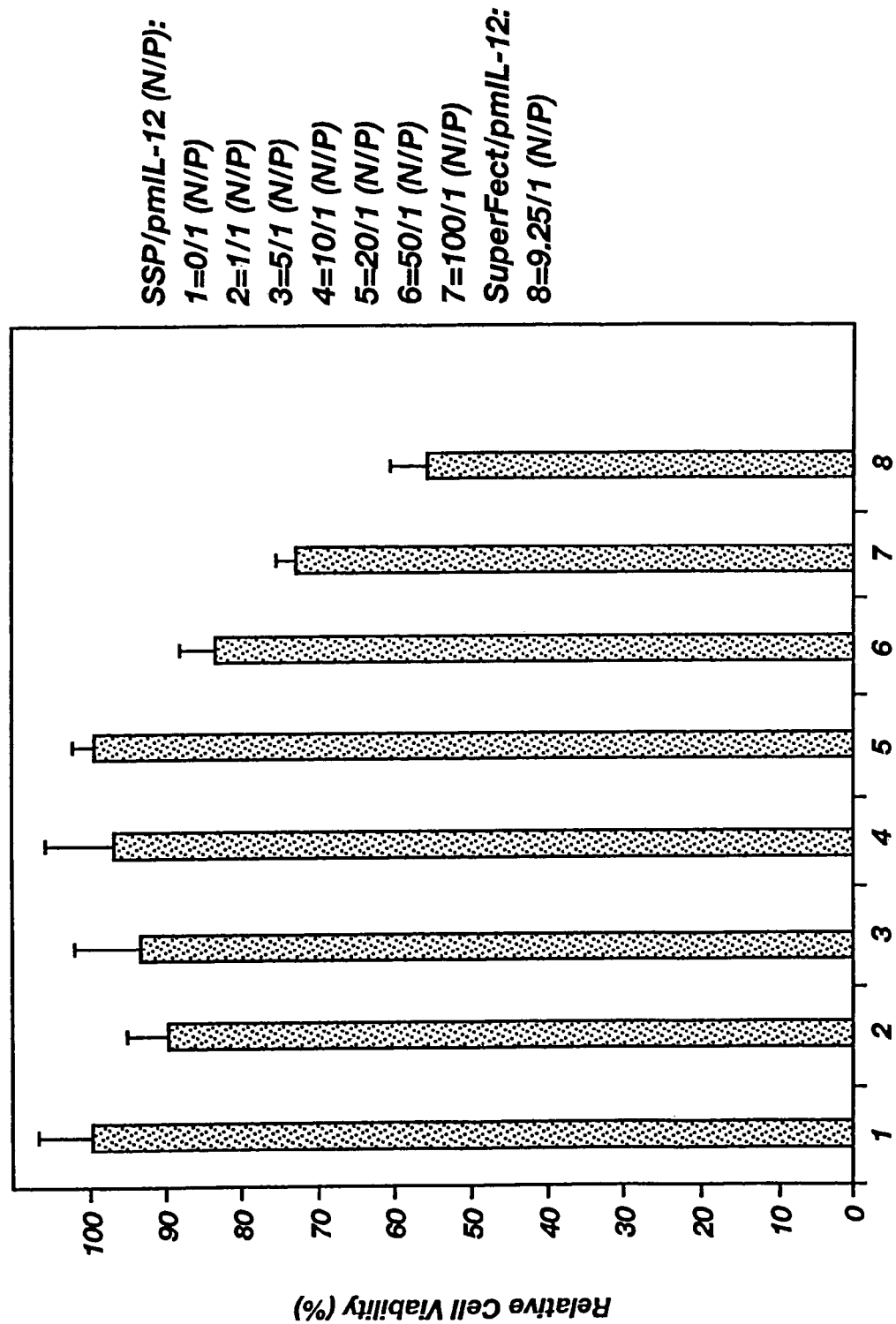
FIG. 6 shows viability of CT-26 colon adenocarcinoma cells after transfection with SSP/p2CMVmIL-12 complexes prepared at various N/P ratios in 5% (w/v) glucose and 0.25 M phosphate buffer, pH 8.0. Naked p2CMVmIL-12 and SuperFect/p2CMVmIL-12 (9.23/1, N/P) were used for comparison. Relative cell viability was at least 80% for all SSP/p2CMVmIL-12 complexes with N/P ratios $\leq 50/1$. In contrast, SuperFect/p2CMVmIL-12 complexes upon transfection resulted in less than 60% cell viability.

SSP/p2CMVmIL-12 complexes prepared according to the procedure of Example 5 were tested for cytotoxicity using MTT assay in CT-26 cells over a wide range of N/P ratios. Commercially available polyamido amine (PAMAM) dendrimer (SuperFect)/p2CMVmIL-12 (6/1, w/w) complexes were used as controls for comparison. SuperFect, a G6 dendrimer has an approximate molecular weight of 30,000 with a total of 140 protonatable amines. SSP/p2CMVmIL-12 complexes were indeed non-toxic to the cells, when formulated at N/P ratio of 50/1 (+/−) and below (FIG. 6). In contrast, SuperFect/p2CMVmmIL-12 were toxic to the cells and the cell viability of CT-26 cells was reduced to less than 60%. Cells treated with Superfect/p2CMVmIL-12 complexes were granulated, and cell debris was quite evident under light microscopy whereas the cell population was unaffected and there was greater than 90% viability for all cells treated with SSP/pDNA complexes up to N/P ratios as high as 50/1. SSP alone was also put to test for its cytotoxicity at various N/P ratios and was found to be non-toxic at the amounts equivalent to those used in N/P ratios 20/1. However, the cell viability decreased to approx. 75% at N/P ratio 50/1.

EXAMPLE 7

In Vitro Transfections

Figure 7:
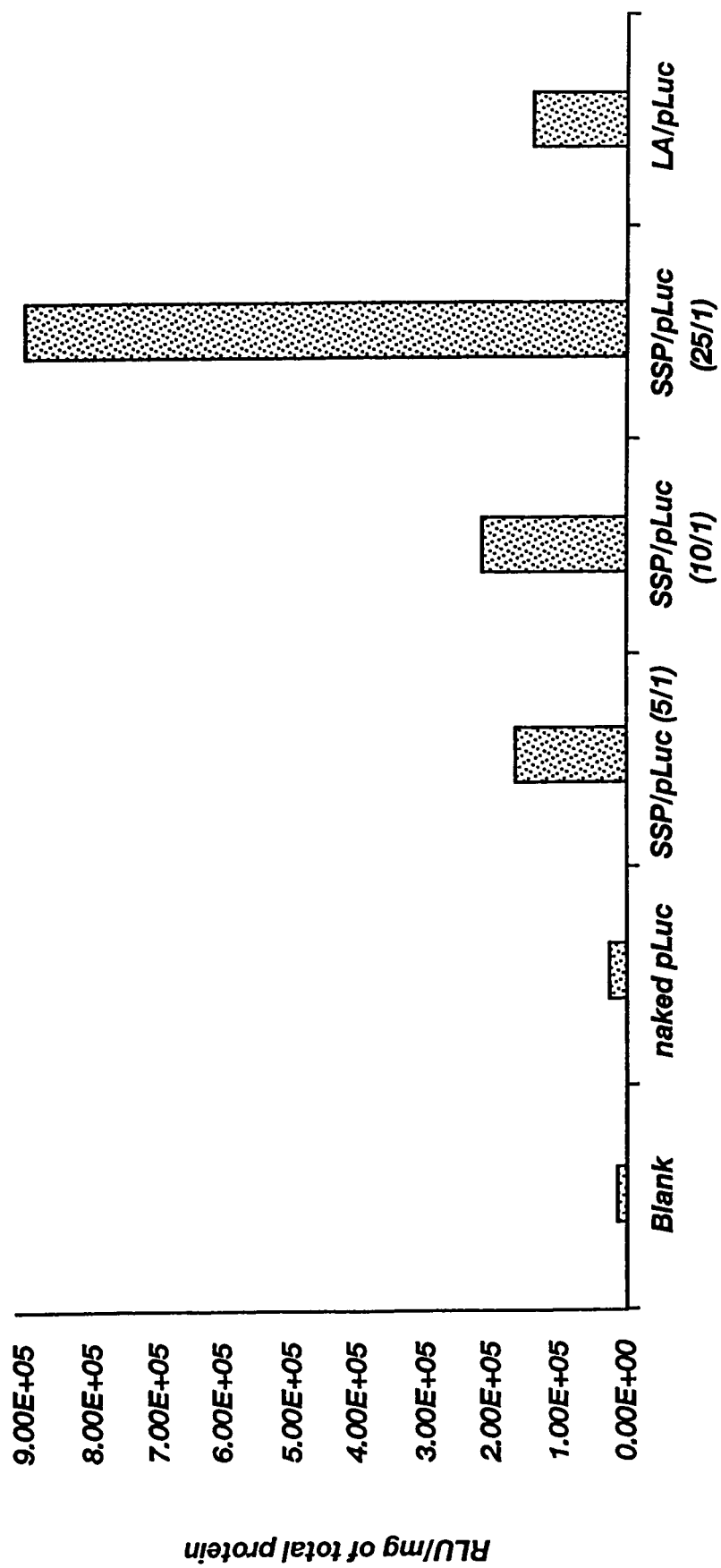
FIG. 7 shows luciferase activity in cultured cells as well as CT-26 subcutaneous tumors 48 hours after transfection. Non-transfected cells were used as negative controls. Luciferase activity is expressed as RLU/mg of total protein.

SSP/pLuc and SSP/p2CMVmIL-12 complexes formulated at various N/P ratios in 5% (w/v) glucose were evaluated for their transfection efficiency in CT-26 colon carcinoma cell lines. In the case of luciferase gene controls, cells were lysed after transfection and the relative light units (RLU) and total protein concentration were determined. SSP/pLuc complexes showed high transfection efficiencies between N/P ratios 20/1 and 50/1. The transfection efficiency increased with the increase in N/P ratios but diminished slightly with ratios 50/1 and above which could possibly be due to cytotoxicity towards CT-26 cells. On visual inspection under light microscope some granulation of cells was found, and cytotoxicity tests indicate that above N/P ratios 50/1 the cell viability is reduced by about 80%, which would account for lower gene expression. As shown in FIG. 7, the RLU values for SSP/pLuc complexes gave several orders of magnitude higher luciferase levels compared to naked pLuc. Peptide sequence used as a control was not effective in mediating transfection and SSP alone did not give any gene expression.

In case of pLuc, CT-26 cells were seeded in 12-well tissue culture plates at $1\times10^5$ cells per/well in 10% FBS containing RPMI 1640 media. Cells achieved 70% confluency within 24 hours, after which they were transfected with SSP/pDNA complexes prepared at different N/P ratios ranging from 5/1 to 50/1 as described above. The total amount of pLuc loaded was maintained constant at 1.5 µg/well and transfection was carried out in the presence of the same serum-containing medium that was used to maintain the cells. The cells were allowed to incubate in the presence of complexes for 4 hours in $CO_2$ incubator followed by replacement of 0.5 ml of RPMI 1640 containing 10% FBS. Thereafter the cells were incubated for additional 48 hours. Cells were lysed using 1× lysis buffer (Promega, Madison, Wis.) after washing with cold PBS. Total protein assays were carried out using BCA protein assay kit (Pierce Chemical Co, Rockford, Ill.). Luciferase activity was measured in terms of relative light units (RLU) using 96 well plate Luminometer (Dynex Technologies Inc, Chantilly, Va.). The luciferase activity was monitored and integrated over a period of 30 secs. The final values of luciferase were reported in terms of RLU/mg total protein (FIG. 7). In all the above experiments, naked pLuc and superfect as well as untreated cultures were used as positive and negative controls, respectively.

In case of p2CMVmIL-12, all transfections were carried out exactly the same way and after 48 hours of incubation the supernatants were collected and stored at −20° C. until further use. Culture supernatants were assayed for mIL-12 p70 using enzyme linked immunosorbent assay (ELISA) kits as suggested by the manufacturer.

In case of cytokine genes, the culture media was collected after transfection and the levels of mIL-12 p70 was determined using ELISA kit BDOptEIA™ for mIL-12 p70 (Pharmingen, San Diego, Calif.), which was used according to the manufacturer's instructions. Briefly, ELISA plates (Nunc, Maxisorp, Denmark) were coated with capture antibody, sealed and kept overnight for antibody binding. The plate was washed several times followed by incubation with assay diluent to block any non-specific binding for one hour. After washing several times, the plate was then incubated with samples and standards for 2 hours. After incubating with detection antibody solution containing avidin-HRP reagent for 1 hour, the substrate solution was added to carry out enzymatic reaction. The reaction was stopped by 2N $H_2SO_4$ and the plate was read at 450 nm using BIO-RAD (model 3550) ELISA reader (Hercules, Calif.). The mIL-12 p70 concentrations were reported in terms of pg/ml and were normalized across different samples.

Figure 8:
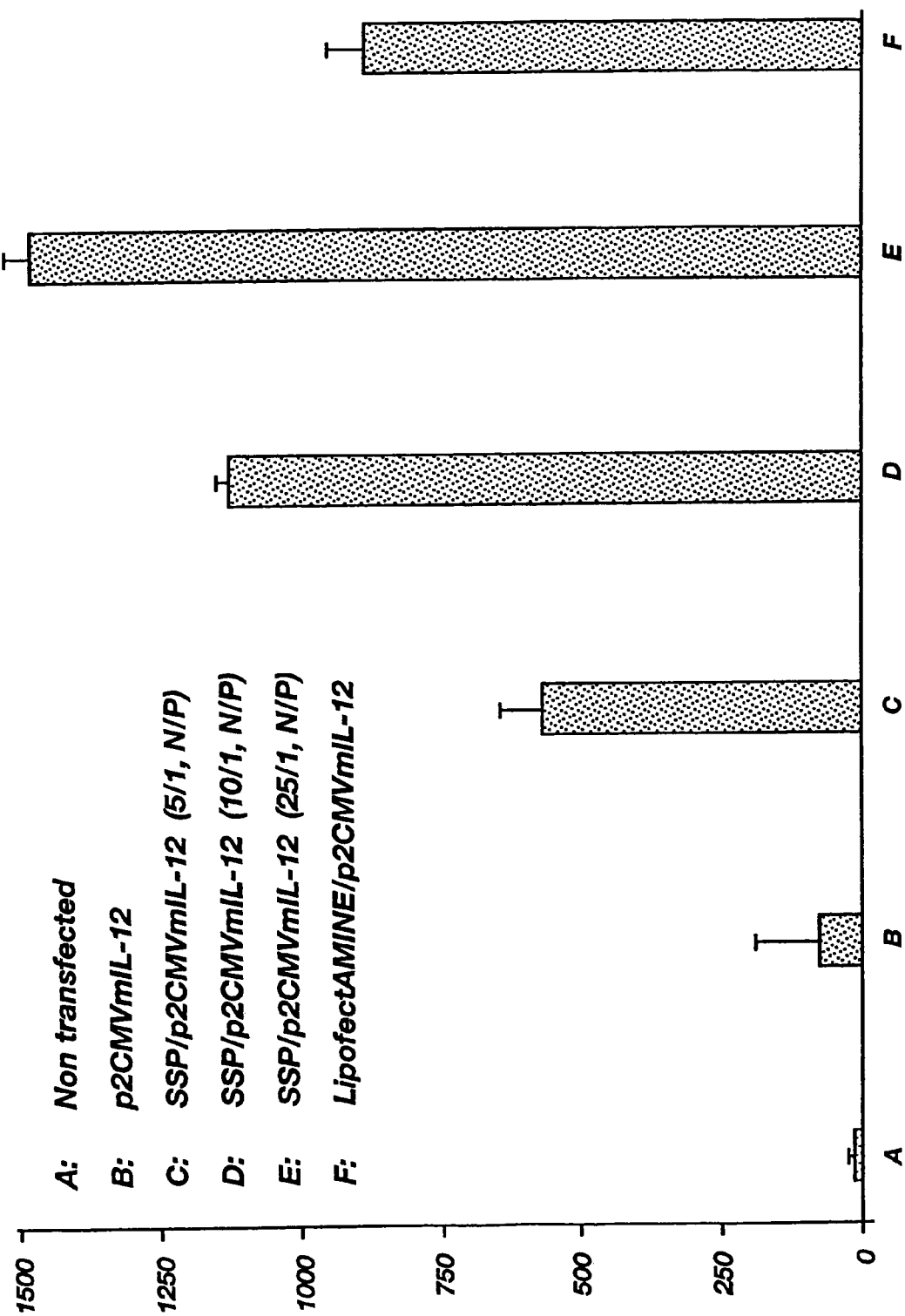
FIG. 8 shows ELISA for mIL-12 levels in cultured CT-26 colon adenocarcinoma cells. Non-transfected cells were used as negative controls.

Trends similar to luciferase transfection followed when a gradient of various N/P ratios $\geq 20/1$ was used. As shown in FIG. 8, the mIL-12 levels for SSP/pmIL-12 complexes were over 20 fold greater than naked p2CMVmIL-12.

Therefore, soluble amphiphilic lipopeptides were synthesized that, in addition to being completely biodegradable, result in high transfection efficiencies without compromising survivability of cells.

The invention claimed is:

1. A plasmid configured for expressing p35 and p40 subunits of interleukin-12 under control of at least one cytomegalovirus promoter, wherein said plasmid is p2CMVmIL-12.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

His Tyr Arg Arg Arg His Cys Ser Arg Arg Arg Leu His
1               5                   10

<210> SEQ ID NO 2
<211> LENGTH: 15
<212> TYPE: PRT
<213> ORGANISM: Artificial Sequence
<220> FEATURE:
<223> OTHER INFORMATION: The cysteine residue of SEQ ID NO:1 was
      replaced with a lysine residue, and histidine residues were added
      to the amino and carboxy termini.

<400> SEQUENCE: 2

His His Tyr Arg Arg Arg His Lys Ser Arg Arg Arg Leu His His
1               5                   10                  15
```